(12) United States Patent
Murphy et al.

(10) Patent No.: US 10,905,328 B2
(45) Date of Patent: Feb. 2, 2021

(54) CONTINUOUS DETECTION AND MONITORING OF HEART ARRHYTHMIA USING BOTH WEARABLE SENSORS AND CLOUD-RESIDENT ANALYSES

(71) Applicant: Verily Life Sciences LLC, Mountain View, CA (US)

(72) Inventors: Mark Murphy, Mountain View, CA (US); Nikhil Bikhchandani, San Francisco, CA (US)

(73) Assignee: Verily Life Sciences LLC, Mountain View, CA (US)

( * ) Notice: Subject to any disclaimer, the term of this patent is extended or adjusted under 35 U.S.C. 154(b) by 142 days.

(21) Appl. No.: 16/184,754

(22) Filed: Nov. 8, 2018

(65) Prior Publication Data

US 2019/0159676 A1 May 30, 2019

Related U.S. Application Data

(60) Provisional application No. 62/592,203, filed on Nov. 29, 2017.

(51) Int. Cl.
*A61B 5/00* (2006.01)
*A61B 5/0464* (2006.01)
(Continued)

(52) U.S. Cl.
CPC .......... *A61B 5/0022* (2013.01); *A61B 5/0006* (2013.01); *A61B 5/0205* (2013.01);
(Continued)

(58) Field of Classification Search
CPC ... A61B 5/0022; A61B 5/7257; A61B 5/0404; A61B 5/0006; A61B 5/7264;
(Continued)

(56) References Cited

U.S. PATENT DOCUMENTS

2014/0257049 A1 9/2014 Soundarapandian et al.
2016/0143585 A1 5/2016 Donnelly et al.

FOREIGN PATENT DOCUMENTS

WO 2011048592 A1 4/2011
WO 2012140559 A1 10/2012
(Continued)

OTHER PUBLICATIONS

Thomas et al., "BioWatch—A Wrist Watch based Signal Acquisition System for Physiological Signals including Blood Pressure", IEEE, , pp. 2286-2289, 2014.
(Continued)

*Primary Examiner* — Scott M. Getzow
(74) *Attorney, Agent, or Firm* — McDonnell Boehnen Hulbert & Berghoff LLP

(57) ABSTRACT

Systems and methods are provided for continuously monitoring a user to determine when cardiovascular events are likely occurring and to responsively provide a prompt to a user to engage in additional physiological assessment of the putative cardiovascular event. Additional assessment can include the user engaging an additional sensor to provide signals that are more accurate, lower noise, or otherwise improved relative to a continuously-monitoring sensor used to initially detect the cardiovascular event. Detection of cardiovascular events includes using a cardiovascular classifier to determine, based on the output of such a continuously-monitoring sensor, whether the event is likely occurring. Such a classifier can be received from a cloud computing service or other remote system based on sensor outputs sent to such a system. Use of such a classifier can facilitate reduced false-positive detection of cardiovascular events based on the continuously-monitoring sensor, and thus reduce extraneous prompts to the user.

20 Claims, 5 Drawing Sheets

(51) Int. Cl.
  *A61B 5/024* (2006.01)
  *A61B 5/0205* (2006.01)
  *A61B 5/0404* (2006.01)
  *A61B 5/11* (2006.01)

(52) U.S. Cl.
  CPC ........ *A61B 5/02416* (2013.01); *A61B 5/0404* (2013.01); *A61B 5/0464* (2013.01); *A61B 5/681* (2013.01); *A61B 5/7221* (2013.01); *A61B 5/7257* (2013.01); *A61B 5/7264* (2013.01); *A61B 5/7282* (2013.01); *A61B 5/1118* (2013.01); *A61B 2560/0242* (2013.01); *A61B 2562/0219* (2013.01)

(58) Field of Classification Search
  CPC ..... A61B 5/7282; A61B 5/681; A61B 5/7221; A61B 5/0464; A61B 5/02416; A61B 5/0205; A61B 2560/0242; A61B 5/1118; A61B 2562/0219
  See application file for complete search history.

(56) References Cited

FOREIGN PATENT DOCUMENTS

| WO | 2015150199 | A1 | 10/2015 |
| WO | 2017003794 | A1 | 1/2017 |
| WO | 2017172272 | A1 | 10/2017 |

OTHER PUBLICATIONS

Perez, "AliveCor unveils Kardia Band, a medical-grade EKG band for Apple Watch", https://techcrunch.com/2016/03/16/alivecor-unveils-kardia-band-a-medical-grade-ekg-band-for-apple-watch/.
Broussard, "AliveCor Announces Apple Watch 'Kardia Band' for Medical Grade EKG Analysis", MacRumors, Mar. 16, 2016, https://www.macrumors.com/2016/03/16/alivecor-apple-watch-kardia-band/.
AliveCor, https://store.alivecor.com.
Zio XT by iRhythm, https://www.irhythmtech.com/.
International Search Report of International Application No. PCT/US18/61747 dated Jan. 28, 2019.

CONTINUOUS DETECTION AND MONITORING OF HEART ARRHYTHMIA USING BOTH WEARABLE SENSORS AND CLOUD-RESIDENT ANALYSES

CROSS-REFERENCE TO RELATED APPLICATION

This application claims priority to U.S. Provisional Patent Application No. 62/592,203, filed Nov. 29, 2017.

BACKGROUND

Unless otherwise indicated herein, the materials described in this section are not prior art to the claims in this application and are not admitted to be prior art by inclusion in this section.

A variety of cardiovascular parameters or other information about the health state of a person can be detected by a wearable device that is mounted to the person's body. Such a wearable device can operate one or more sensors to continuously detect information about the person's body. Such continuous monitoring can provide an increased amount of data to improve the determination of information about the person's health state, e.g., by increasing a confidence level of a health state determination. Additionally, by continuously monitoring the person across extended periods of time and/or across a variety of activities of the person, rare physiological events can be detected. Such rare events could be indicative of a serious health condition, e.g., atrial fibrillation.

SUMMARY

Some embodiments of the present disclosure provide a wearable device, including: (i) a housing that is mountable to an external body surface of a wearer; (ii) a first electrical contact that is disposed on the housing and that contact contacts the external body surface when the housing is mounted on the external body surface; (iii) a second electrical contact; (iv) a sensor; (v) a user interface; (vi) a transceiver; and (vii) a controller that includes a computing device. The controller is programmed to perform operations including: (a) detecting, using the sensor during a first period of time, a first signal; (b) transmitting, using the transceiver, an indication of the first signal to a remote server; (c) using the transceiver to receive, from the remote server, an indication of a cardiovascular classifier based on the first signal; (d) detecting, using the sensor during a second period of time, a second signal; (e) using the cardiovascular classifier to determine that the second signal is indicative of a cardiovascular event; (f) responsive to determining that the second signal is indicative of the cardiovascular event, using the user interface to provide a prompt; and (g) after using the user interface to provide the prompt, detecting an electrocardiographic waveform from voltage fluctuations between the first electrical contact and the second electrical contact.

Some embodiments of the present disclosure provide a method for operating a wearable device. The wearable device includes: (a) a housing that is mountable to an external body surface of a wearer; (b) a first electrical contact that is disposed on the housing and that contacts the external body surface when the housing is mounted on the external body surface; (c) a second electrical contact; (d) a user interface; and (e) a transceiver. The method includes: (i) detecting, using the sensor of the wearable device during a first period of time, a first signal, (ii) transmitting, using the transceiver, an indication of the first signal to a remote server; (iii) using the transceiver to receive, from the remote server, an indication of a cardiovascular classifier based on the first signal; (iv) detecting, using the sensor during a second period of time, a second signal; (v) using the cardiovascular classifier to determine that the second signal is indicative of a cardiovascular event; (vi) responsive to determining that the second signal is indicative of the cardiovascular event, using the user interface to provide a prompt; and (vii) after using the user interface to provide the prompt, detecting an electrocardiographic waveform from voltage fluctuations between the first electrical contact and the second electrical contact.

These as well as other aspects, advantages, and alternatives, will become apparent to those of ordinary skill in the art by reading the following detailed description, with reference where appropriate to the accompanying drawings.

DETAILED DESCRIPTION

Figure 1A:
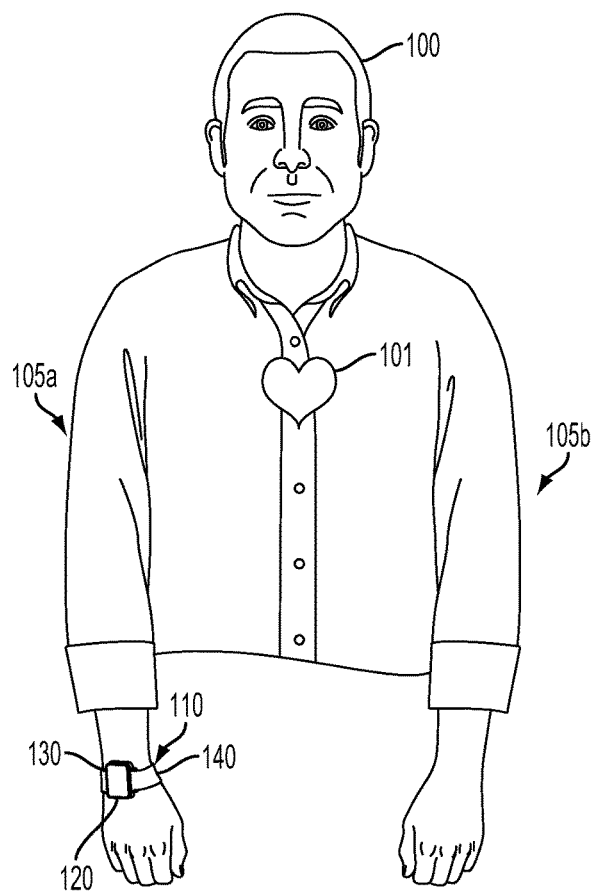
FIG. 1A is a view of a person wearing an example wearable device.

In the following detailed description, reference is made to the accompanying figures, which form a part hereof. In the figures, similar symbols typically identify similar components, unless context dictates otherwise. The illustrative embodiments described in the detailed description, figures, and claims are not meant to be limiting. Other embodiments may be utilized, and other changes may be made, without departing from the scope of the subject matter presented herein. It will be readily understood that the aspects of the present disclosure, as generally described herein, and illustrated in the figures, can be arranged, substituted, combined, separated, and designed in a wide variety of different configurations, all of which are explicitly contemplated herein.

I. Overview

It can be beneficial to continuously monitor a person for the occurrence of certain health events, e.g., cardiovascular events. For example, it could be beneficial to monitor for ventricular or atrial fibrillation, tachycardia, bradycardia, or other arrhythmic events. Detection of such events via continuous monitoring can facilitate prompt emergency medical attention, administration of a drug or other therapy, or improved detection of information about the cardiovascular event. For example, in response to determining that a continuously-monitored signal is indicative that a cardiovascular event is occurring, a person could be prompted to perform a diagnostic activity, to apply pressure to a device or sensor (e.g., to improve a noise level or other property of signals generated by the sensor), to touch an electrode of a device to facilitate detection of electrocardiographic signals, or to perform some other task or activity. Such additional signals or information about the cardiovascular event could be used to diagnose a health condition, to determine a dose of a drug or other treatment, to determine information about the efficacy of a drug, to determine information about a disease (e.g., a population distribution of properties of the disease), or to determine some other useful information.

In order to detect the occurrence of such events of interest (e.g., cardiovascular events), one or more sensors could be incorporated into a wearable device and worn by a wearer. The one or more sensors could be operated to detect pulse rates, time-varying blood volume in subsurface vasculature, electrocardiographic signals, the acceleration or rotation of a body part, ambient light levels, or other signals that could be used to determine whether a cardiovascular event is occurring. The determination of whether a cardiovascular event is occurring could involve use of a cardiovascular classifier to determine whether one or more sensor signals are indicative of the cardiovascular event. For example, one or more sensor signals could be used to determine an activity of the wearer, and the determined activity could be used in combination with some other sensor signal to determine whether a cardiovascular event is occurring. When the device, using the cardiovascular classifier, determines that a cardiovascular event is occurring, the device could operate to prompt the wearer to perform some action, e.g., to touch an electrode of the device to facilitate detection of an electrocardiographic waveform, to perform a diagnostic activity.

However, the incidence of false positives (i.e., situations wherein a signal appears to be indicative of a cardiovascular event, but no cardiovascular event is occurring) can result in unnecessary prompts, reducing wearer compliance with the prompts or causing other unwanted effects. Further, the incidence of false negatives (i.e., situation wherein a cardiovascular event is occurring but a system does not detect the event) can result in reduced collection of event-related data, delayed medical treatment, or other unwanted effects. In order to reduce the incidence of false positives and/or false negatives, a cardiovascular classifier could be generated based on extensive data from one or more devices (e.g., from devices collecting data from one or more wearers), data from clinical data acquisition systems, or other data sources. Further, the cardiovascular classifier used by a wearable device could be updated over time, e.g., based on signals detected by the wearable device.

Accessing such extensive sources of data (e.g., from clinical systems, from many other wearable devices) and using such data to generate a cardiovascular classifier could require an amount of data storage, an amount of processor power, access to remote databases, or other factors that are difficult or impractical to provide in the wearable device itself. Instead, a wearable device could upload sensor data to a cloud computing service, a computer at a physician's office or hospital, or some other remote server. The remote server could then use the sensor data from the wearable device, along with additional data (e.g., data from other wearable devices, data from clinical data acquisition systems, data from previous clinical studies or other sources of population data), to generate a cardiovascular classifier. The remote server could then transmit the determined cardiovascular classifier to the wearable device, and the wearable device could use the cardiovascular classifier to determine whether sensor signals generated by the wearable device are indicative of a cardiovascular event. The wearable device could also receive updated cardiovascular classifiers from the remote server, e.g., cardiovascular classifiers that have been updated based on additional sensor data received from the wearable device, from other wearable devices, or from some other source.

II. Cardiovascular Classifiers and Detection of Cardiovascular Events

A wearable device, e.g., a wrist-mountable device, could include one or more sensors configured to detect physical variables (e.g., to illuminate a portion of subsurface vasculature and detect a volume of blood in the portion of subsurface vasculature based on a detected intensity of responsively emitted light) that are related to the occurrence or non-occurrence of a cardiovascular event of interest. Such cardiovascular events could include atrial or ventricular fibrillation, tachycardia, bradycardia, or other arrhythmias, acute hypertension or hypotension, incidents of postural orthostatic tachycardia syndrome, incidents of clinical or subclinical cardiac arrest or ischemia, extra heart beats, or other events of interest. It could be beneficial to use such a wearable device to continuously monitor a wearer in order to detect the occurrence of such events. Such detection could permit more prompt delivery of medical care, timed application of a drug or other medical treatment, detection of additional information about rare events, or some other beneficial applications.

A variety of physiological or other signals related to a cardiovascular event or to some physiological event or process of interest could be detected and used to determine whether such an event is occurring as described herein. In some examples, such signals could be directly related to the event or process of interest, e.g., a photoplethysmographic signal, electrocardiographic signal, or other signal related to pulse timing, pulse rate, electrical activity of the heart, or some other process that is related to tachycardia or some other arrhythmic condition. Additionally or alternatively, the signals could be related to factors surrounding the process or event of interest, or could provide a context that could facilitate detection of an event of interest. For example, an ambient light level, an orientation, acceleration, or rotation of a body segment over time, a galvanic skin resistance, or some other signals could be used to determine an activity of a wearer, e.g., to determine whether the wearer is resting, walking, sleeping, eating, exercising, or engaging in some other activity. Such a determined activity could then be used to determine whether a sensor signal is indicative of a cardiovascular event.

For example, a particular detected pulse rate, pulse rate variability, or other signal of interest could be within a range of expected values if a wearer is determined to be exercising. However, if the particular detected pulse rate, pulse rate variability, or other signal of interest is detected while the wearer is sleeping, resting, or otherwise engaged in a non-strenuous activity, it could be indicative that the wearer is experiencing tachycardia, myocardial infarction, or some other cardiovascular event. In such an example, the wearer could be prompted to seek medical attention, to take a drug, to facilitate detection of electrocardiographic or other signals of interest related to the event, or to take some other action.

When a device has determined (using a cardiovascular classifier or other algorithm) that the output of one or more sensors is indicative of a cardiovascular event, the device may responsively perform some additional operations. For example, the device could prompt a user to seek medical attention, prompt the user to perform a diagnostic task (e.g., to interact with a user interface of the device, to perform a sit-and-stand task), prompt the user to interact with the device in some way (e.g., to facilitate detection of an electrocardiographic waveform or other signal of interest), operate an additional sensor of the device (e.g., a sensor whose operation has a high power budget) or operate a sensor in a higher-power mode, or perform some other operations.

The device could prompt a user to interact with a sensor of the device in order to permit the detection of a signal of interest and/or to improve a noise level, accuracy, or other quality of a detected signal of interest. For example, the user could be prompted to apply pressure to the device to improve a level of coupling between a sensor and skin of the wearer, to align a sensor with a part of the wearer's body, to control a degree of perfusion of subsurface vasculature, to control a pressure applied to subsurface vasculature (e.g., to detect a blood pressure), or to perform some other action.

As an example, a wearable device could be configured to mount to a first wrist (e.g., the left wrist) of the wearer and to have a first electrical contact configured to contact a first skin location on the first wrist. The wearable device could further include a second electrical contact configured to be contacted by a second skin location of the wearer. That is, the wearer could move a portion of the wearer's body (e.g., a right hand) proximate to the wearable device such that a second skin location (e.g., a finger, hand, or wrist location of the arm of the wearer opposite the arm to which the wearable device is mounted) is in contact with the second electrical contact of the wearable device. In this way, the wearable device could enable periodic extraction of electrocardiographic signals from voltage fluctuations between the two skin locations (e.g., between a wrist location of the left arm and a finger location of the right arm). Such a wearable device could be configured in the form of a wristwatch or other wrist-mounted device (i.e., having a central housing (on or within which could be mounted first and/or second electrical contacts) mounted to the wrist by e.g., a strap or band configured to encircle the wrist) and could include means for performing additional functions, e.g., indicating a time and/or pulse rates to the wearer, prompting the wearer to contact the electrode(s), etc.

FIG. 1A illustrates such an example wearable device 110 mounted to a wrist of a first arm 105a of a wearer 100 during a first period of time. The wearable device 110 includes a housing 120 mounted to the wrist of the first arm 105a by a mount 140 (e.g., a strap or band). The wearable device further includes first (not shown) and second 130 electrical contacts. The first electrical contact is disposed on an inside (i.e., wrist-facing) side of the housing 120 and configured to contact skin at a first external body surface (i.e., skin of the wrist of the first arm 105a) when the housing 120 is mounted on the wrist of the first arm 105a. The second electrical contact 130 is configured to be contacted by skin of a second external body surface (e.g., by finger, hand, wrist, or other skin of a second arm 105b of the wearer 100). The wearable device 110 additionally includes electronics (e.g., a signal conditioner or other elements of a sensor, not shown) electrically connected to the first and second 130 electrical contacts and configured to extract an electrocardiographic waveform (related to a cardiovascular pulse of the heart 101 of the wearer 100) from voltage fluctuations between the first and second 130 electrical contacts.

Figure 1B:
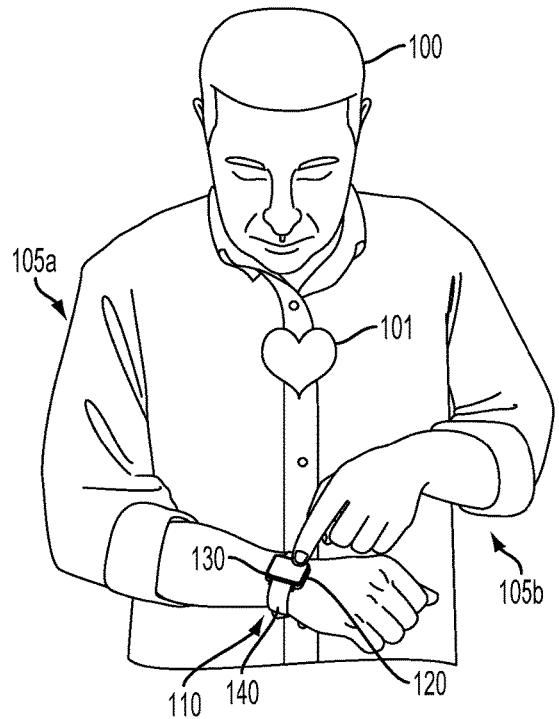
FIG. 1B is a view of the person and wearable device illustrated in FIG. 1A, when the user is contacting the wearable device with a finger.

FIG. 1B illustrates the wearable device 110 and wearer 100 during a second period of time when the wearer 100 is positioning skin of a finger of the second arm 105b in contact with the second electrical contact 130. In this state, electronics (e.g., a signal conditioner) of the wearable device 110 could extract an electrocardiographic waveform related to the cardiovascular pulse of the wearer's 100 heart 101 during the second period of time from voltage fluctuations between the first and second 130 electrical contacts.

Figure 1C:
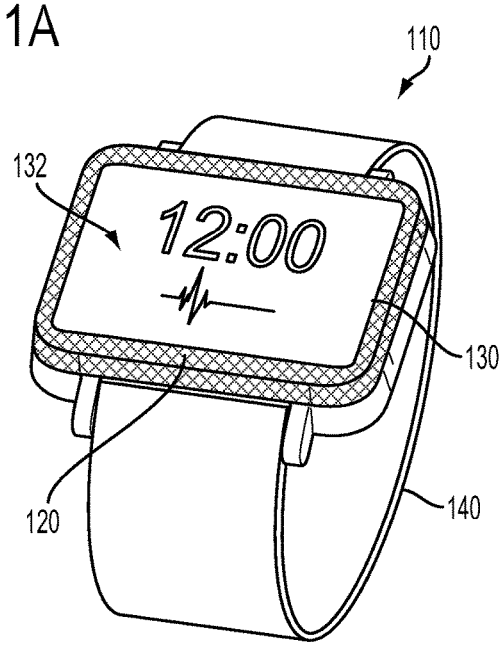
FIG. 1C is a perspective view of an example wearable device.

FIG. 1C illustrates the wearable device 110 in detail. The housing 120 has an outside surface that is away from the first external surface of the body and an inside surface (not shown) that is toward and/or in contact with the first external surface of the body when the housing 120 is positioned on the first external surface of the body. A user interface 132 is disposed on the outside surface of the housing 120. The second electrical contact 130 is disposed along an edge of the outside surface of the housing 110d completely enclosing the user interface 132. Other configurations of a wearable device as described herein are anticipated.

Such signals could be detected and assessed to determine whether a signal of interest can be reliably determined from a sensor. This could include determining a power level of the detected signal, a signal to noise ratio of the detected signal (e.g., a power in frequency bands corresponding to a cardiovascular pulse or other signal of interest divided by total signal power), a power of the signal within one or more frequency bands (e.g., within frequency bands related to noise content of the signal), a variability of a pulse rate or pulse period determined based on the signal, a quality and/or presence of a feature in the signal (e.g., a QRS complex in the signal), or some other determination related to whether a signal of interest can be reliably determined from the sensor output. Additionally or alternatively, some additional variable related to the signal of interest could be detected and used to determine whether a signal of interest can be reliably determined from the sensor output. For example, an impedance between electrodes of an electrocardiogram sensor, a pressure or force between a sensor and a skin surface, or some other variables related to the use of a sensor to detect the signal of interest could be detected and used to determine whether the signal of interest can be reliably detected using the sensor.

A cardiovascular classifier can be used to determine whether one or more sensor signals are indicative of the cardiovascular event of interest. A cardiovascular classifier can apply thresholds, filters, pattern-matching templates, linear or nonlinear kernels or transforms, finite state machines, statistical inference, or other algorithms or techniques, individually or in combination, to determine whether a cardiovascular event is occurring, or is likely occurring, based on one or more sensor signals detected from a wearer's body and/or from an environment of the wearer. Such a determination could include generating a binary output related to the presence of the cardiovascular event and/or generating a likelihood or other value corresponding to the probability, in view of one or more sensor signals, that the cardiovascular event is occurring.

Using a cardiovascular classifier to determine whether a signal is indicative of a cardiovascular event could include transforming the signal in some way and/or determining some representative information about the signal. For example, the signal could be bandpass filtered, lowpass filtered, highpass filtered, applied to a moving-average filter, convolved with a matching filter, thresholded, applied to a polynomial, or filtered or modified in some other way. The signal could be resampled or separated into discrete overlapping or non-overlapping portions (e.g., into individual portions corresponding to respective different heart beats). The signal could be transformed, e.g., using the Fourier transform, the Laplace transform, a wavelet transform, or some other transformation to generate frequency components or other transformed information about the signal. Pulses, peaks, heart beats, electrocardiographic complexes, or other features could be detected within the signal and used to generate information about the signals, e.g., to determine the presence or timing of the features, to determine a shape of the features, to determine a rate of occurrence of a feature and/or to determine a variability of such a rate over time, to determine a deviation of the shape of the features from a template, or to determine some other information about features in the signal.

Using a cardiovascular classifier to determine whether a signal is indicative of a cardiovascular event could include using a linear or nonlinear kernel or matrix to generate an output based on a vector of inputs related to the sensor signal (e.g., based on a vector of samples of the signal, based on a vector of frequency components of the signal, based on a vector of properties of pulses or other features within the signal). For example, linear or nonlinear principal components analysis, independent component analysis, a support vector machine, or some other algorithm could be used to determine one or more output values based on a signal. Such output values could then be thresholded, applied to a sigmoid or other nonlinear function, or used in some other manner according to the cardiovascular classifier to determine whether the sensor signal is indicative of the cardiovascular event of interest.

Using a cardiovascular classifier to determine whether a signal is indicative of a cardiovascular event could include using pattern matching to determine whether the signal, or some information determined from the signal, is indicative of the cardiovascular event. This could include determining a degree similarity between the sensor signal, frequency components of the sensor signal, an output of another element of the classifier (e.g., the output of a principal components analysis), or some other information related to the signal and a template pattern. Such a degree of similarity could be used to determine that the cardiovascular event is occurring and/or to determine the likelihood that the cardiovascular event is occurring. Additionally or alternatively, a template pattern could be convolved with the signal and/or with an output determined from the signal and the result of the convolution could be used to determine whether the signal is indicative of the cardiovascular event (e.g., if the output of the convolution exceeds a threshold value for more than a threshold duration). Additionally or alternatively, such pattern matching could be used to detect features within the sensor signal and/or to determine information about such features (e.g., to determine a character of the deviation of such features from a template pattern).

Using a cardiovascular classifier to determine whether a signal is indicative of a cardiovascular event could include using multiple signals to detect the occurrence or likelihood of occurrence of the cardiovascular event. This could include applying two or more signals to respective elements of the cardiovascular classifier (e.g., to respective principal components analyses) and combining the outputs of the elements (e.g., by element-wise multiplication of outputs of respective different principal components analyses) or combining the information from two different signals in some other way (e.g., by convolving the signals together). Additionally or alternatively, one or more of the signals could be used to set a filter parameter, finite state machine state, operating mode, internal variable, or other property of operation of the cardiovascular classifier which could then be used to determine whether some additional or alternative one or more of the signals is indicative of the cardiovascular event. For example, one or more signals (e.g., accelerometer signals, gyroscope signals, ambient light signals) could be used to determine an activity of the wearer (e.g., sleeping, exercising, walking, sitting, eating). The cardiovascular classifier could then determine, based on the detected activity, whether some other sensor signal is indicative of the cardiovascular event It can be beneficial to reduce the false-positive detection of such cardiovascular events (e.g., to improve wearer compliance with performing diagnostic tasks or providing improved sensor signals) and to reduce the false-negative non-detection of such events (e.g., to prevent loss of data about an event of interest). To improve the detection of cardiovascular events, based on continuous monitoring of one or more related physiological properties or processes related thereto, the cardiovascular classifier could be determined and/or updated based on sensor data from one or more wearable devices or from other sources of information (e.g., clinical data acquisition systems). The cardiovascular classifier for a particular device of a particular wearer could be determined based on days, months, or years of sensor data detected by one or more wearable device(s) of the particular wearer. The cardiovascular classifier for a particular device of a particular wearer could also be determined based on data from other persons (e.g., data from wearable devices of other wearers). For example, the cardiovascular classifier could be determined based on information from clinical data acquisition systems (e.g., Holter monitors) that are applied and operated by clinicians and/or from a population of wearers using respective wearable devices as described herein.

The cardiovascular classifier could be updated over time, based on additional sensor signals received from one or more wearable devices or from some other systems (e.g., clinical data acquisition systems). Such updates could occur semi-continuously or according to some other timing. The cardiovascular classifier could be updated based on signals used to confirm that a particular sensor signal was indicative of a cardiovascular event. For example, a first instance of a cardiovascular signal could be used to determine that a first sensor signal is indicative of a cardiovascular event. In response to that determination, a wearable device could provide a prompt to a wearer such that an electrocardiographic waveform or other signal related to the putative based cardiovascular event is detected. The detected electrocardiographic waveform or other related signal could then be used to determine whether the first sensor signal was actually indicative of the cardiovascular event and that determination could be used to update the cardiovascular classifier.

Using such extensive and/or various data to generate and/or update a cardiovascular classifier could require an amount of data storage, an amount of processor power, access to remote databases, or other factors such that it is not feasible for the cardiovascular classifier to be generated and/or updated by a wearable device. Rather, such a wearable device could upload sensor data to a cloud computing service, a computer at a physician's office or hospital, or some other remote server. The remote server could then use the sensor data from the wearable device, along with additional data (e.g., data from other wearable devices, data from clinical data acquisition systems, data from previous clinical studies or other sources of population data), to generate a cardiovascular classifier. The remote server could then transmit the determined cardiovascular classifier to the wearable device, and the wearable device could use the cardiovascular classifier to determine whether future sensor signals generated by the wearable device are indicative of a cardiovascular event. The wearable device could also receive updated cardiovascular classifiers from the remote server, e.g., cardiovascular classifiers that have been updated based on additional sensor data received from the wearable device, from other wearable devices, or from some other source.

III. Example Devices

Figure 2:
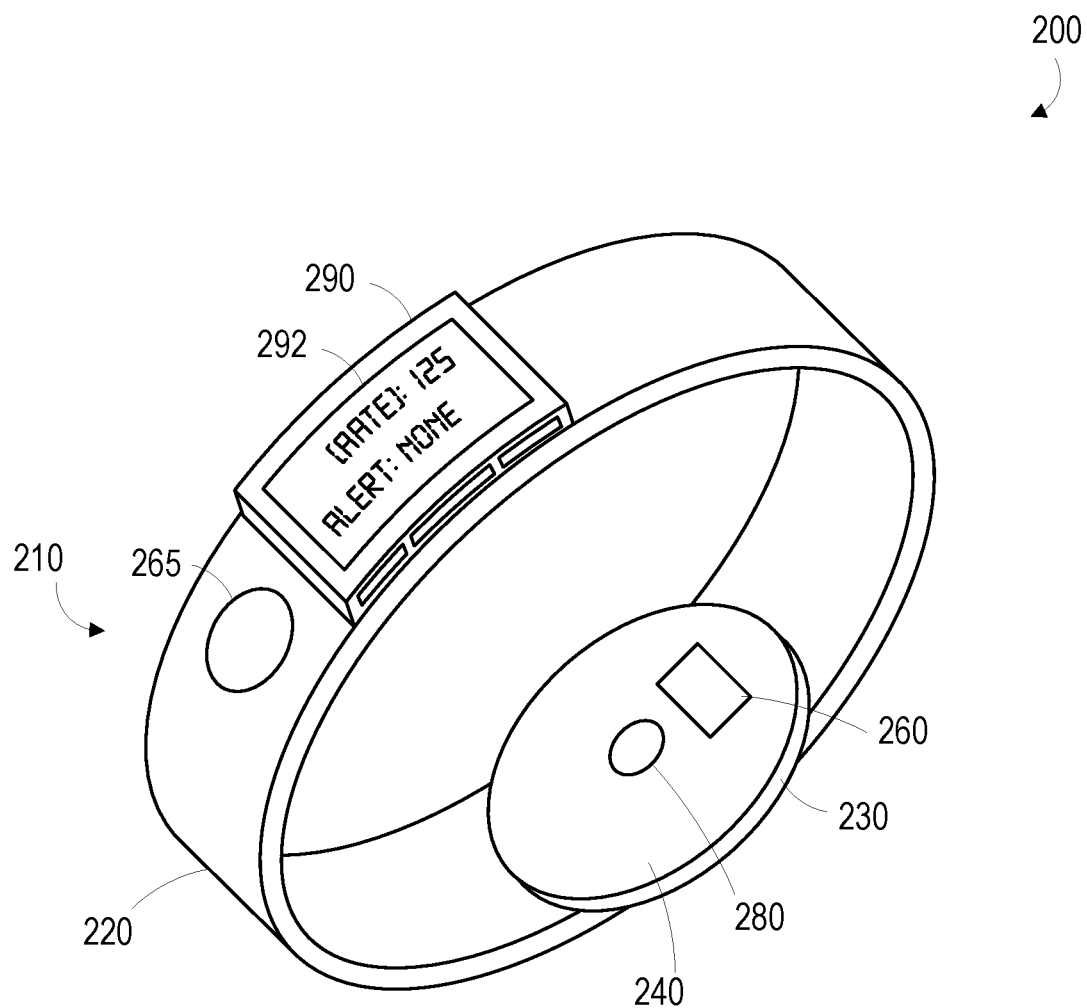
FIG. 2 is a perspective view of an example wearable device.

One or more devices or systems could be configured to detect a signal, apply a cardiovascular classifier to the detected signal to determine whether a cardiovascular event is likely occurring, and, responsive to determining that a cardiovascular event is occurring, provide a prompt to a user (e.g., to touch an electrode on the device, to perform a clinical assessment or other activity) or perform some other activity (e.g., detect an electrocardiographic signal using two or more electrodes or electrical contacts of a wearable device). An example of a wearable device 200 that can perform such operations, or other operations described herein, is illustrated in FIG. 2.

The term "wearable device," as used in this disclosure, refers to any device that is capable of being worn at, on or in proximity to a body surface, such as a wrist, ankle, waist, chest, or other body part. In order to take in vivo measurements in a non-invasive manner from outside of the body, the wearable device may be positioned on a portion of the body where a signal related to a cardiovascular event may be detected (e.g., proximate a portion of subsurface vasculature or some other tissue containing pulsatile blood flow, proximate one or more skin locations from which an electrocardiographic signal may be extracted), the qualification of which will depend on the type of detection system used. The device may be placed in close proximity to skin or tissue, but need not be touching or in intimate contact therewith. A mount 210, such as a belt, wristband, ankle band, etc. can be provided to mount the device at, on or in proximity to the body surface. The mount 210 may prevent the wearable device from moving relative to the body to reduce measurement error and noise. In one example, shown in FIG. 2, the mount 210, may take the form of a strap or band 220 that can be worn around a part of the body. Further, the mount 210 may be an adhesive substrate for adhering the wearable device 200 to the body of a wearer.

A measurement platform 230 is disposed on the mount 210 such that it can be positioned on the body where subsurface vasculature is easily observable or where some other signal of interest may be detected. An inner face 240 of the measurement platform is intended to be mounted facing to the body surface. The measurement platform 230 may house first sensor 280, which may be configured to detect one or more signals related to occurrence of a cardiovascular event of interest (e.g., atrial or ventricular tachycardia, bradycardia, or fibrillation, acute hypotension, acute hypertension, or some other event related to the cardiovascular system of a person). For example, the first sensor 280 may include an optical sensor that is configured to detect a degree of absorption of light at one or more wavelengths by blood in a portion of subsurface vasculature over time (e.g., by illuminating the portion of subsurface vasculature and detecting an intensity or other properties of light responsively reflected by, scattered by, or otherwise emitted from the portion of subsurface vasculature). In another example, the first sensor 280 may include an accelerometer, a pressure sensor, or some other sensor configured to detect a blood pressure in the portion of subsurface vasculature, to detect a displacement of the skin surface related to changes in the volume or pressure of blood in the portion of subsurface vasculature or to motion of a body part (e.g., during exercise, walking, sleeping, or other activities), or to detect some other physical variable related to occurrence or non-occurrence of a cardiovascular event.

The measurement platform 230 may include multiple such sensors, and the signals detected using the sensor(s) could be substantially continuously related to a cardiovascular event or signal related thereto (e.g., related to a cardiovascular pulse or other physiological signal or process related to the cardiovascular pulse) or could be intermittently related to the cardiovascular event or signal related thereto (e.g., when the absolute or relative (to a target tissue, e.g., skin surface, portion of subsurface vasculature) motion of the sensor is minimal, when the sensor is in consistent contact with skin or with some other tissue). Further, the measurement platform 230 may include elements of sensors that are configured to operate to detect a signal that is related to the cardiovascular event when a wearer performs some action. For example, the measurement platform 230 includes a first electrode 260 that is configured to be in contact with skin of the wrist when the wearable device 200 is mounted to the wrist. The wearable device also includes a second electrode 265 that is disposed on the band 220 and that can be contacted by skin of an opposite arm (e.g., skin of a fingertip) of a wearer. When the device 200 is mounted to a wrist such that the first electrode 260 is in contact with skin of the wrist and the second electrode 265 is being contacted by skin of the opposite arm, an electrocardiographic signal could be detected by the device 200 using the electrodes 260, 265. The electrocardiographic signal could then be used to confirm whether the cardiovascular event is occurring, to detect some additional information about the cardiovascular event, or to facilitate some other application.

The wearable device 200 may also include a user interface 290 via which the wearer of the device may receive one or more recommendations, prompts, alerts, or other indications generated either from a remote server or other remote computing device, or from a processor within the device. For example, the user interface 290 could be used, in response to determining that a cardiovascular event is occurring or is likely to be occurring, to prompt the user to touch the second electrode 265 such that an electrocardiographic signal could be detected to provide additional information about such a cardiovascular event. The indications could be any indication that can be noticed by the person wearing the wearable device. For example, the indication could include a visual component (e.g., textual or graphical information on a display), an auditory component (e.g., an alarm sound), and/or tactile component (e.g., a vibration). Further, the user interface 290 may include a display 292 where a visual indication of the alert, prompt, or recommendation may be displayed. The display 292 may further be configured to provide an indication of the measured physiological parameters, for instance, a determined cardiovascular pulse rate.

A wearable device as described herein (e.g., wearable device 210) could be modular. That is, one or more components of such a wearable device could be replaceable, extensible, and/or otherwise reconfigurable to add and/or remove capabilities of the wearable device. For example, a wearable device could include a housing containing a battery, a communications interface, a touchscreen user interface, and general-purpose electronics to enable a variety of applications of a wearable device. The wearable device could further include a modular mount configured to mount the housing to an external body surface and to enable some applications of the wearable device, e.g., by including one or more sensors. For example, a first modular mount could be configured to mount the housing around a wrist of a wearer and to enable extraction of an electrocardiographic waveform from voltage fluctuations between the arms of a wearer by providing a second electrical contact on an outside surface of the mount (e.g., an outer surface of a frame encircling the housing) to complement a first electrical contact provided by the housing on an inside surface of the housing. A second modular mount could be configured to mount the housing around the chest of a wearer and to enable detection of breathing patterns of the wearer by providing a strain sensor in a band of the mount that encircles the chest of the wearer. Elements of such a modular device could be electrically connected via, e.g., spring-loaded contacts.

Figure 3:
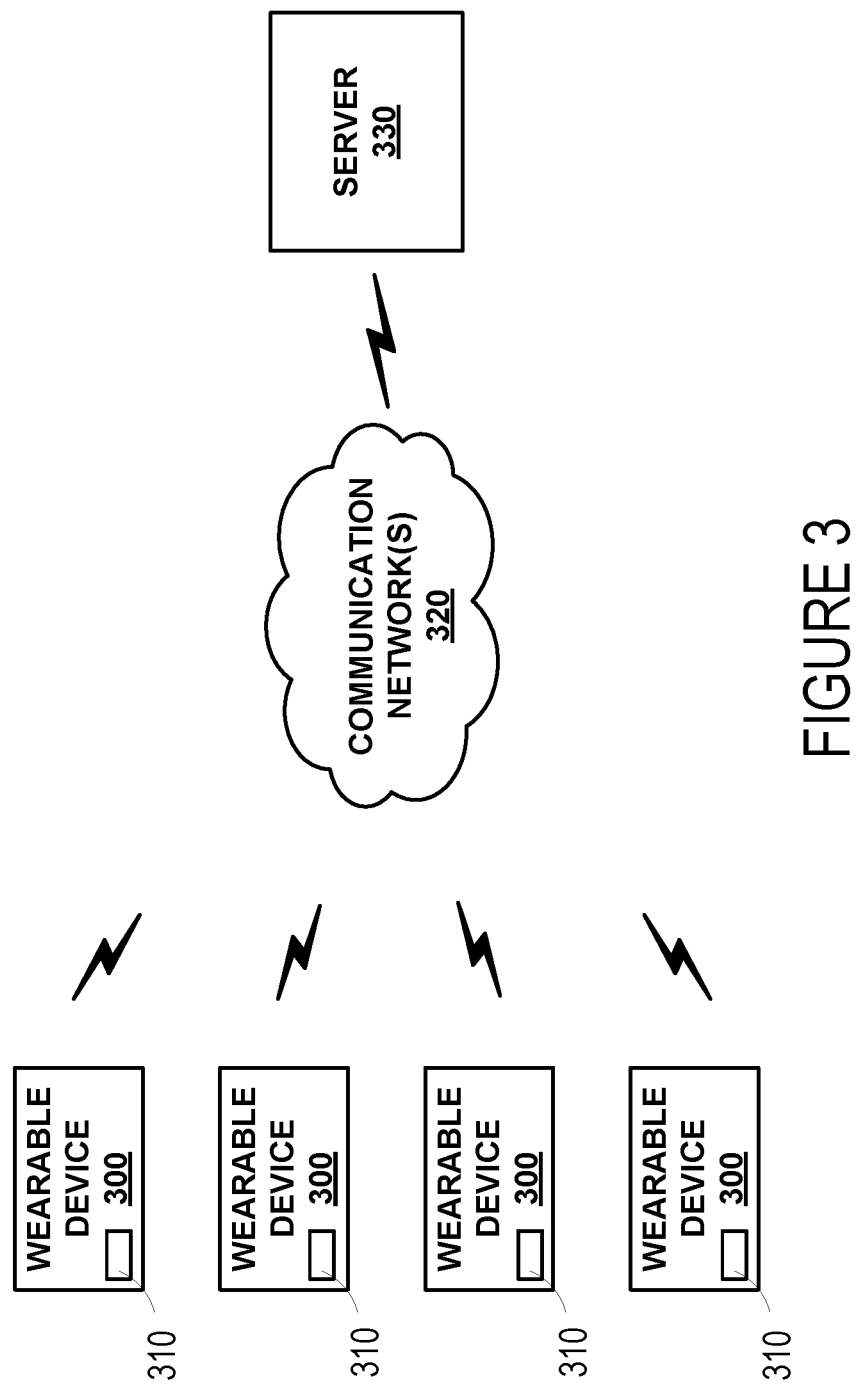
FIG. 3 is a block diagram of an example system that includes a plurality of wearable devices in communication with a server.

FIG. 3 is a simplified schematic of a system including one or more wearable devices 300. The one or more wearable devices 300 may be configured to transmit data via a communication interface 310 over one or more communication networks 320 to a remote server 330. In one embodiment, the communication interface 310 includes a wireless transceiver for sending and receiving communications to and from the server 330. In further embodiments, the communication interface 310 may include any means for the transfer of data, including both wired and wireless communications. For example, the communication interface may include a universal serial bus (USB) interface or a secure digital (SD) card interface. Communication networks 320 may be any one of may be one of: a plain old telephone service (POTS) network, a cellular network, a fiber network and a data network. The server 330 may include any type of remote computing device or remote cloud computing network. Further, communication network 320 may include one or more intermediaries, including, for example wherein the wearable device 300 transmits data to a mobile phone or other personal computing device, which in turn transmits the data to the server 330.

In addition to receiving communications from the wearable device 300, such as collected physiological parameter data and data regarding health state as input by the user, the server may also be configured to gather and/or receive either from the wearable device 300 or from some other source, information regarding a wearer's overall medical history, environmental factors and geographical data. For example, a user account may be established on the server for every wearer that contains the wearer's medical history. Moreover, in some examples, the server 330 may be configured to regularly receive information from sources of environmental data, such as viral illness or food poisoning outbreak data from the Centers for Disease Control (CDC) and weather, pollution and allergen data from the National Weather Service. Further, the server may be configured to receive data regarding a wearer's health state from a hospital or physician. Such information may be used in the server's decision-making process, such as recognizing correlations and in generating clinical protocols.

Additionally, the server may be configured to gather and/or receive the date, time of day and geographical location of each wearer of the device during each measurement period. Such information may be used to detect and monitor spatial and temporal spreading of diseases. As such, the wearable device may be configured to determine and/or provide an indication of its own location. For example, a wearable device may include a GPS system so that it can include GPS location information (e.g., GPS coordinates) in a communication to the server. As another example, a wearable device may use a technique that involves triangulation (e.g., between base stations in a cellular network) to determine its location. Other location-determination techniques are also possible.

The server 330 may also be configured to make determinations regarding cardiovascular events of a user based on information received from one or more of the wearable devices 300 that are associated with the user. This could include receiving signals detected by multiple sensors of a single wearable device 300 and/or receiving signals from multiple devices 300 and using the received signals to determine some information about cardiovascular events of a user, e.g., about the existence, timing, or other properties of one or more such events, predictive properties or features of one or more sensor signals in relation to such events, or some other information. The server 330 could also determine information about the sensor signal(s) that could be used by one or more of the devices 300 to determine, based on such sensor signals, whether a cardiovascular event is occurring. For example, the server 330 could determine pattern-matching templates, filter cutoffs, parameters of a predictive algorithm, or some other information related to a cardiovascular classifier that could be transmitted to one of the devices 300. Such a cardiovascular classifier could then be used by the device 300 to predict, based on signals generated by one or more sensors of the device 300, to predict whether a cardiovascular event is occurring. The server 330 could generate such a cardiovascular classifier based on information received from the particular device 300 and/or based on information received from a population of devices 300. Further, the server 330 may periodically update such a cardiovascular classifier (e.g., based on additional sensor signals received from the device 300) and send the updated classifier to the device 300.

The server may also be configured to make determinations regarding drugs or other treatments received by a wearer of one or more of the devices 300 and, at least in part, the cardiovascular event data, detected electrocardiographic signals, and/or the indicated health state of the user. From this information, the server may be configured to derive an indication of the effectiveness of the drug or treatment. For example, if a wearer is prescribed a drug intended to treat tachycardia, but the server receives data from the wearable device(s) indicating (based on determined pulse rates) that the wearer's heart rate has remained elevated over a certain number of measurement periods, the server may be configured to derive an indication that the drug is not effective for its intended purpose for this wearer.

Further, some embodiments of the system may include privacy controls which may be automatically implemented or controlled by the wearer of the device. For example, where a wearer's collected physiological parameter data and health state data are uploaded to a cloud computing network for trend analysis by a clinician, the data may be treated in one or more ways before it is stored or used, so that personally identifiable information is removed. For example, a user's identity may be treated so that no personally identifiable information can be determined for the user, or a user's geographic location may be generalized where location information is obtained (such as to a city, ZIP code, or state level), so that a particular location of a user cannot be determined.

Additionally or alternatively, wearers of a device may be provided with an opportunity to control whether or how the device collects information about the wearer (e.g., information about a user's medical history, social actions or activities, profession, a user's preferences, or a user's current location), or to control how such information may be used. Thus, the wearer may have control over how information is collected about him or her and used by a clinician or physician or other user of the data. For example, a wearer may elect that data, such as cardiovascular classifiers or collected electrocardiographic signals, collected from his or her device may only be used for generating an individual baseline and recommendations in response to collection and comparison of his or her own data and may not be used in generating a population baseline or for use in population correlation studies.

IV. Example Electronics Platform

Figure 4:
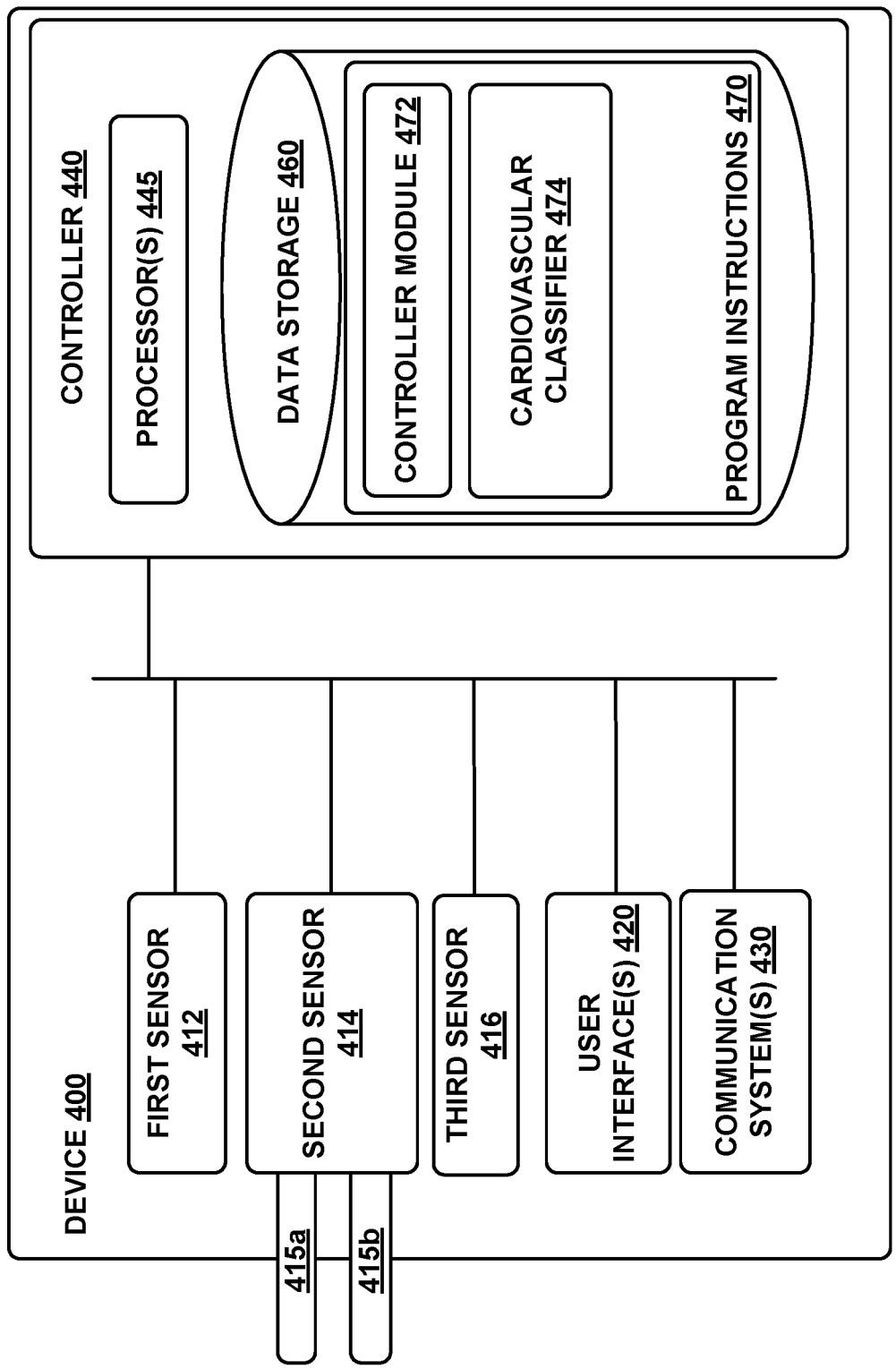
FIG. 4 is a functional block diagram of an example device.

FIG. 4 is a simplified block diagram illustrating the components of a device 400, according to an example embodiment. Device 400 may take the form of or be similar to the devices 110, 200 shown in FIGS. 1A, 1B, 1C and 2. That is, device 400 may take the form of a wrist-mountable or otherwise body-mountable device. Device 400 may also take other forms, e.g., could take the form of a device configured to be maintained in proximity to an environment of interest (e.g., a body part) by a user or operator of the device 400 or by a frame or other supporting structure. Device 400 could also take the form of a device configured to signals of interest from some other environment, for example, a body of an animal or some other environment containing a parameter or variable that contains an oscillating pattern having a frequency or rate that could be detected according to the methods described herein. Device 400 also could take other forms.

In particular, FIG. 4 shows an example of a device 400 having a first sensor 412, a second sensor 414, a third sensor 416, a user interface 420, communication system(s) 430 for transmitting data to a remote system, and a controller 440. The components of the device 400 may be disposed on a mount or on some other structure for mounting the device to enable stable detection of one or more signals related to a cardiovascular event (e.g., related to a cardiovascular pulse rate) or other process of interest, for example, around a wrist of a wearer such that signals related to a portion of subsurface vasculature or other target tissue are detectable.

Controller 440 may be provided as a computing device that includes one or more processors 445. The one or more processors 445 can be configured to execute computer-readable program instructions 470 that are stored in the computer readable data storage 460 and that are executable to provide the functionality of a device 400 described herein.

The computer readable data storage 460 may include or take the form of one or more non-transitory, computer-readable storage media that can be read or accessed by at least one processor 445. The one or more computer-readable storage media can include volatile and/or non-volatile storage components, such as optical, magnetic, organic or other memory or disc storage, which can be integrated in whole or in part with at least one of the one or more processors 445. In some embodiments, the computer readable data storage 460 can be implemented using a single physical device (e.g., one optical, magnetic, organic or other memory or disc storage unit), while in other embodiments, the computer readable data storage 460 can be implemented using two or more physical devices.

The first 412, second 414, and third 416 sensors are configured to detect respective first, second, and third signals. As noted elsewhere herein, the first sensor 412 could detect a signal that is substantially continuously related to a cardiovascular pulse or other physiological properties or processes of a person such that the first signal can be used substantially continuously to estimate whether a specified cardiovascular event (e.g., an instance of atrial or ventricular tachycardia, fibrillation, bradycardia, or some other arrhythmia) is occurring. The second sensor 414 could detect a second signal that may be intermittently related to the cardiovascular event such that the second signal can be used to determine some information about the cardiovascular event (e.g., to verify that the event is occurring, to determine a electrocardiographic waveform of the heart during the event). For example, the second sensor 414 could include two (or more) electrical contacts or electrodes 415*a*, 415*b* that, when a wearer contacts the electrodes 415*a*, 415*b* of the second sensor 414 with skin of the wearer, could be used to detect an electrocardiographic signal related to the operation of the wearer's heart.

The first 412, second 414, and third 416 sensors could be provided on or within a single housing of the device 400 or within multiple housings (e.g., connected using a cable or other interconnection). The first 412, second 414, and third 416 sensors could include any of the types of sensors described elsewhere herein to detect signals that are at least intermittently related to a cardiovascular event or to some other property or process of interest.

The program instructions 470 stored on the computer readable data storage 460 may include instructions to perform any of the methods described herein. For instance, in the illustrated embodiment, program instructions 470 include a controller module 472 and a cardiovascular classifier 474.

The controller module 472 can include instructions for operating the first 412, second 414, and third 416 sensors. For example, the controller module 472 may include instructions for operating a light source and light sensor of the first sensor 412 at a plurality of points in time to obtain a respective plurality of samples of a photoplethysmographic signal. In another example, the third sensor could include at least one of an accelerometer or a gyroscope and the controller module 472 may include instructions for operating the third sensor 416 to measure signals related to a cardiovascular event or to some other signal or process of interest, e.g., to detect the motion and/or orientation of a body segment to which the third sensor 416 is mounted or otherwise mechanically coupled. The controller module 472 may include instructions for operating one or more of the sensors 412, 414, 416 to detect a signal that is not directly related to a cardiovascular event or other signal or interest but that may be related to the operation of the sensors 412, 414, 416 to detect such signals, e.g., to detect an impedance between electrodes that may be used, by the second sensor 414, to detect an electrocardiographic signal. In some examples, the controller module 472 may operate an analog-to-digital converter (ADC) to sample one or more signals (e.g., amplifier outputs) generated by the first 412, second 414, and/or third 416 sensors to obtain sets of samples of the signals detected during one or more periods of time.

The controller module 472 could further include instructions for determining that a signal detected by one of the sensors 412, 414, 416 is related to a signal of interest (e.g., an electrocardiographic signal) during a particular period of time. This could include detecting the presence or some other quality of features (e.g., QRS complexes of an electrocardiographic signal, peaks of a photoplethysmographic signal) in the signal, determining a degree of variability of pulse timing or pulse rates determined from the signal, determining a signal-to-noise ratio or other noise information about the signal, detecting a pressure applied to an external surface of the device 400, or using some other methods. For example, the controller module 472 could include instructions to determine whether first and second electrical contacts of the second sensor 414 are in contact with skin and/or that an ECG waveform can be extracted from voltage fluctuations between such electrical contacts and to responsively extract an ECG waveform. This could include analyzing voltage fluctuations between the electrical contacts to determine whether the voltage fluctuations contain ECG waveforms. Additionally or alternatively, this could include actively or passively sensing an effective resistance and/or capacitance between the electrical contacts and further determining that the sensed resistance and/or capacitance corresponds to the electrical contacts being in contact with skin.

The controller module 472 can also include instructions for operating a user interface 420. For example, controller module 472 may include instructions for displaying data collected by the controller module 472, for presenting prompts to perform diagnostic tasks or other actions (e.g., contacting an electrode of the second sensor 414 to facilitate detection of an electrocardiographic signal), or for providing some other indications. Further, controller module 472 may include instructions to execute certain functions based on inputs accepted by the user interface 420, such as inputs accepted by one or more buttons or touchscreen displays disposed on the user interface.

The cardiovascular classifier 474 may include instructions for analyzing data (e.g., signals detected by the sensor(s) 412, 414, 416) to determine whether a cardiovascular event is occurring (e.g., to determine that a signal received from the sensor(s) is indicative of the cardiovascular event). In particular, the cardiovascular classifier 474 may include instructions for determining spectral contents, detecting features (e.g., heart beats), determining pulse rates or pulse timings, applying kernel methods (e.g., principal components analysis or independent components analysis kernels), for generating a priori or a posteriori probabilities, or for performing some other analyses related to determining, based on one or more sensor signals, whether a cardiovascular event is occurring. In particular, the cardiovascular classifier 474 may include algorithmic parameters, PCA or ICA kernels, polynomial coefficients, threshold values, templates for pattern matching, filter coefficients, or other information that could be used to determine whether a particular sensor signal or signals is indicative of a cardiovascular event. In some examples, the cardiovascular classifier 474 may include instructions for determining a particular activity of the user (e.g., exercising, sleeping, walking, sitting, eating) and determining whether a sensor signal is indicative of the cardiovascular event could include making such a determination based on the determined activity of the user (e.g., selecting a threshold value based on the determined activity, and applying the selected threshold value to a determined pulse rate to determine whether tachycardia or some other cardiovascular arrhythmic event is occurring).

Some of the program instructions of the controller module 472 and the cardiovascular classifier 474 may, in some examples, be stored in a computer-readable medium and executed by a processor located external to the device 400. For example, the device 400 could be configured to operate one or both of the sensors 412, 414, 416 (or to otherwise generate or obtain a plurality of samples of a signal related to a cardiovascular event) and then transmit related data to a remote server, which may include a mobile device, a personal computer, the cloud, or any other remote system, for further processing (e.g., for the detection of cardiovascular events and/or properties or signals related thereto using methods described herein).

User interface 420 could include indicators, displays, buttons, touchscreens, head-mounted displays, and/or other elements configured to present information about the device 400 to a user and/or to allow the user to operate the device 400. Additionally or alternatively, the device 400 could be configured to communicate with another system (e.g., a cellphone, a tablet, a computer, a remote server) and to present elements of a user interface using the remote system. The user interface 420 could be disposed proximate to the sensors 412, 414, 416 or other elements of the device 400 or could be disposed away from other elements of the device 400 and could further be in wired or wireless communication with the other elements of the device 400. The user interface 420 could be configured to allow a user to specify some operation, function, or property of operation of the device 400. The user interface 420 could be configured to present a determined pulse rate, cardiovascular event, or some other health state of a wearer of the device 400, or to present some other information to a user. For example, the user interface 420 could be operated, in response to determining that a cardiovascular event is occurring or is likely occurring, to prompt the wearer to perform some action related to the cardiovascular event (e.g., to perform a diagnostic task, to seek medical attention, to take a drug, to touch an electrical contact of the device 400). Other configurations and methods of operation of a user interface 420 are anticipated.

Communication system(s) 430 may also be operated by instructions within the program instructions 470, such as instructions for sending and/or receiving information via a wired or wireless medium using a transceiver, which may be disposed on or in the device 400. The communication system(s) 430 can optionally include one or more oscillators, mixers, frequency injectors, etc. to modulate and/or demodulate information on a carrier frequency to be transmitted and/or received by the antenna. In some examples, the device 400 is configured to indicate an output from the controller 440 by transmitting an electromagnetic or other wireless signal according to one or more wireless communications standards (e.g., Bluetooth, WiFi, IRdA, ZigBee, WiMAX, LTE) using communication system(s) 430. In some examples, the communication system(s) 430 could include one or more wired communications interfaces and the device 400 could be configured to indicate an output from the controller 440 by operating the one or more wired communications interfaces according to one or more wired communications standards (e.g., USB, FireWire, Ethernet, RS-232).

In some examples, obtained samples of a signal or other physiological property or parameter of interest, determined information about cardiovascular events, or other information generated by the device 400 may additionally be input to a cloud network and be made available for download by a user's physician. Analyses may also be performed on the collected data, such as estimates of pulse rate variability, arrhythmia, determinations of post-surgical treatment or rehabilitation regimens, and/or efficacy of drug treatment regimens, in the cloud computing network and be made available for download by physicians or clinicians. Further, collected information from individuals or populations of device users may be used by physicians or clinicians in monitoring efficacy of a surgical intervention or other treatment.

V. Illustrative Methods

Figure 5:
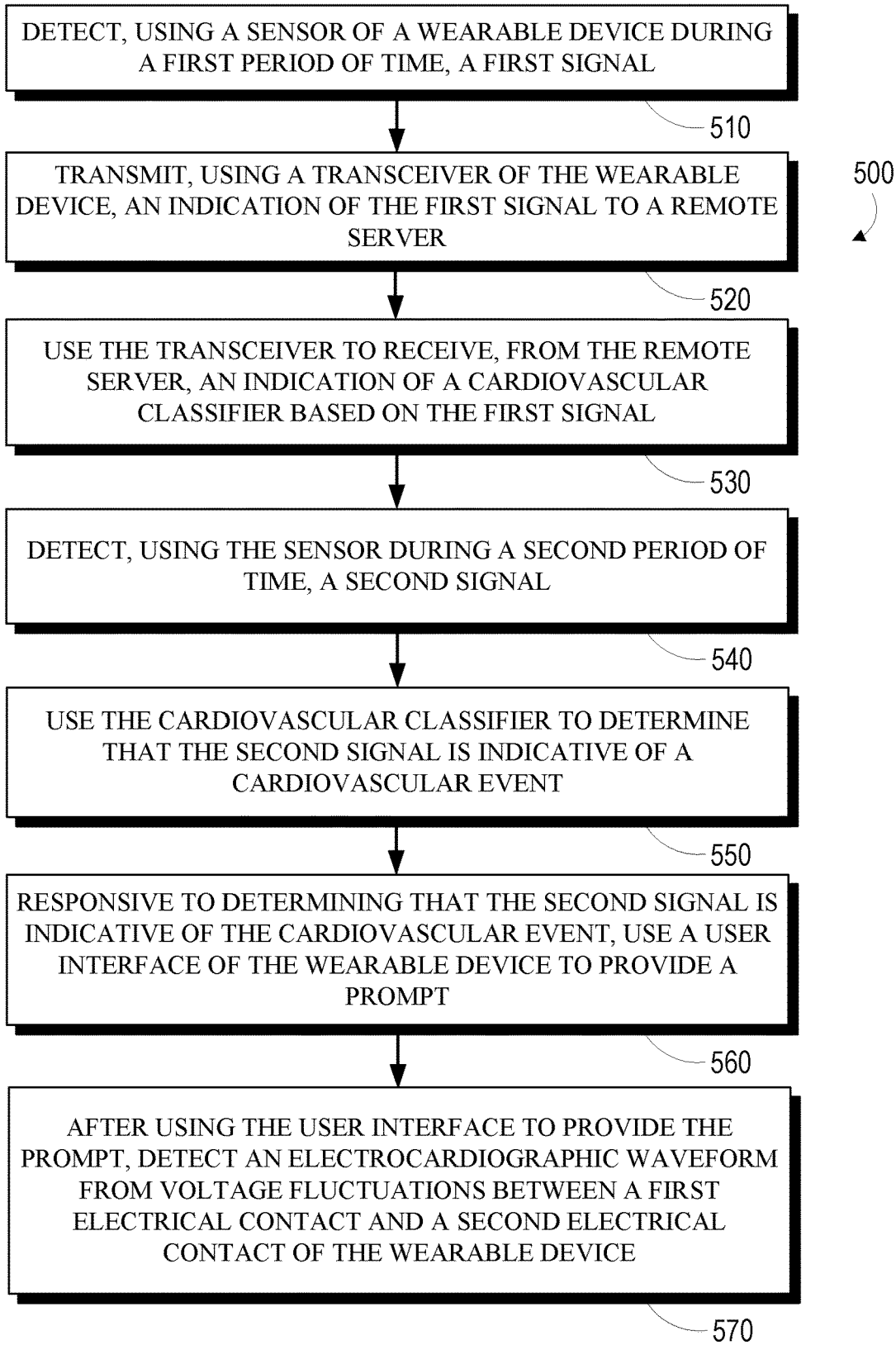
FIG. 5 is a flow chart of an example method.

FIG. 5 is a flowchart of a method 500 for operating a wearable device. The wearable device includes: (i) a housing that is mountable to an external body surface of a wearer; (ii) a sensor; (iii) a first electrical contact that is disposed on the housing and that contacts the external body surface when the housing is mounted on the external body surface; (iv) a second electrical contact; (v) a user interface; and (vi) a transceiver.

The method 500 includes detecting, using the sensor during a first period of time, a first signal (510). This could include operating a sensor to detect an intensity of light, a pattern of constructive and destructive interference in received light, a pressure, a temperature, an acceleration, a displacement, a color, a flow rate, or some other property related to a cardiovascular event, e.g., using a pressure sensor, a light sensor, a light emitter, a tonometer, an ultrasonic transducer, or some other sensing means. In some examples, detecting the first signal could include detecting a plethysmographic signal, i.e., a signal related to a volume of blood in a portion of subsurface vasculature. Detecting such a signal could include operating a light source to illuminate a portion of subsurface vasculature and operating a light sensor to detect an intensity or other property of light responsively scattered by, reflected by, or otherwise emitted from the portion of subsurface vasculature.

The method 500 additionally includes transmitting, using the transceiver, an indication of the first signal to a remote server (520). This could include transmitting the signal via a wired or wireless medium, e.g., via a cellular data network. The indication of the first signal could be transmitted substantially continuously (e.g., every few seconds as the first signal is detected). Additionally or alternatively, the indication of the first signal could be transmitted periodically, e.g., once a day, when the device is connected to a wired communication medium, when the device has access to one or more specified wireless access points or other specified communications medium. For example, the device could operate to detect and log the first signal throughout the day and to upload the logged data to the remote server when the device is connected to a charging station (e.g., at night) and/or when the device has access to a user's home wireless network.

The method 500 additionally includes using the transceiver to receive, from the remote server, an indication of a cardiovascular classifier based on the first signal (530). This could include receiving the indication of the cardiovascular classifier via a wireless or wired communication medium. The received indication of the cardiovascular classifier could include an indication of the identity or parameters of an algorithm, source code or other instructions that describe the cardiovascular classifier and that can be executed by a processor of the device, a binary file that could be executed by a processor of the device to implement the cardiovascular classifier, or some other information related to the cardiovascular classifier. The received indication of the cardiovascular classifier could include a full description of the cardiovascular classifier and/or could include a description of differences between the cardiovascular classifier and a previous cardiovascular classifier (e.g., a cardiovascular classifier previously received by the device).

The method 500 additionally includes detecting, using the sensor during a second period of time, a second signal (540). The method 500 further includes using the cardiovascular classifier to determine that the second signal is indicative of a cardiovascular event (550). In some examples, this could include using a signal detected, during the second period of time, by a further sensor (e.g., by an accelerometer and/or a gyroscope) to determine a particular activity of the wearer during the second period of time. Determining whether the second signal is indicative of a cardiovascular event could include making such a determination based on the determined particular activity of the wearer.

The method 500 further includes, responsive to determining that the second signal is indicative of the cardiovascular event, using the user interface to provide a prompt (560). This could include providing, via the user interface, a visual indication, an auditory indication, a tactile indication, or any other sort of indication that could be perceived by a wearer to indicate that the wearer could contact an electrical contact of the device and/or engage in some other activity.

The method 500 additionally includes, after using the user interface to provide the prompt, detecting an electrocardiographic waveform from voltage fluctuations between the first electrical contact and the second electrical contact (570). This could include determining whether both of the electrical contacts are in contact with skin of the wearer and/or whether an electrocardiographic waveform can be detected from the voltage fluctuations between the first electrical contact and the second electrical contact and, responsive to such a determination, detecting the electrocardiographic waveform from the voltage fluctuations. For example, the device could apply a voltage and/or current to the electrical contacts to detect an impedance between the electrical contacts. Additionally or alternatively, the device could determine whether a QRS complex or other signals indicative of an electrocardiographic waveform are present in the voltage fluctuations between the first electrical contact and the second electrical contact.

The method 500 could include additional steps or elements in addition to those illustrated in FIG. 5. For example, the method 500 could include transmitting an indication of the detected electrocardiographic waveform to an external system, e.g., to the remote server. The method 500 could include determining a pulse rate or other information about the wearer based on signals detected by the device and/or the method 500 could include operating the user interface to provide an indication of such determined information. The method 500 could include transmitting additional signals detected by the sensor to the remote server and responsively receiving an updated cardiovascular classifier from the remote server. The method 500 could include, subsequent to receiving such an updated cardiovascular classifier, using the received updated cardiovascular classifier to determine whether further signals generated by the sensor are indicative of a cardiovascular event. The method 500 could include determining, based on the detected electrocardiographic waveform, that the cardiovascular event is occurring. The method 500 could further include, responsive to such a determination, using the user interface to provide an indication of the cardiovascular event (e.g., an indication of the identity and/or properties of the event, an alert to seek medical attention, an alert to take a drug or other therapy). Additional and/or alternative steps of the method 500 are anticipated.

VI. Conclusion

Where example embodiments involve information related to a person or a device of a person, the embodiments should be understood to include privacy controls. Such privacy controls include, at least, anonymization of device identifiers, transparency and user controls, including functionality that would enable users to modify or delete information relating to the user's use of a product.

Further, in situations in where embodiments discussed herein collect personal information about users, or may make use of personal information, the users may be provided with an opportunity to control whether programs or features collect user information (e.g., information about a user's medical history, pulse rates, health states, or other information about the user, a user's preferences, or a user's current location), or to control whether and/or how to receive content from the content server that may be more relevant to the user. In addition, certain data may be treated in one or more ways before it is stored or used, so that personally identifiable information is removed. For example, a user's identity may be treated so that no personally identifiable information can be determined for the user, or a user's geographic location may be generalized where location information is obtained (such as to a city, ZIP code, or state level), so that a particular location of a user cannot be determined. Thus, the user may have control over how information is collected about the user and used by a content server.

The particular arrangements shown in the Figures should not be viewed as limiting. It should be understood that other embodiments may include more or less of each element shown in a given Figure. Further, some of the illustrated elements may be combined or omitted. Yet further, an exemplary embodiment may include elements that are not illustrated in the Figures.

Moreover, it is particularly noted that while devices, systems, methods, and other embodiments are described herein by way of example as being employed to detect cardiovascular events of a human body, it is noted that the disclosed devices, systems, and methods can be applied in other contexts as well. For example, detection systems configured to use a first sensor (or set of sensors, or sensor operating mode) to detect an event, and responsive to such detection, use a second sensor (or set of sensors, or sensor operating mode) to detect some information related to the event, to provide a prompt related to the event, or to perform some other operation(s) related to the event may be included in wearable (e.g., body-mountable) and/or implantable devices. In some contexts, such a detection system is situated to be substantially encapsulated by bio-compatible polymeric material suitable for being in contact with bodily fluids and/or for being implanted.

In other examples, devices, systems, and methods disclosed herein may be applied to detect the incidence or other properties of events in environments that are not in or on a human body. For example, detection systems disclosed herein may be included in devices used to detect cardiovascular or other physiological events of an animal.

Additionally, while various aspects and embodiments have been disclosed herein, other aspects and embodiments will be apparent to those skilled in the art. The various aspects and embodiments disclosed herein are for purposes of illustration and are not intended to be limiting, with the true scope and spirit being indicated by the following claims. Other embodiments may be utilized, and other changes may be made, without departing from the spirit or scope of the subject matter presented herein. It will be readily understood that the aspects of the present disclosure, as generally described herein, and illustrated in the figures, can be arranged, substituted, combined, separated, and designed in a wide variety of different configurations, all of which are contemplated herein.

What is claimed is:

1. A wearable device, comprising:
a housing, wherein the housing is mountable to an external body surface of a wearer;
a first electrical contact disposed on the housing, wherein the first electrical contact contacts the external body surface when the housing is mounted on the external body surface;
a second electrical contact;
a sensor;
a user interface;
a transceiver; and
a controller, wherein the controller comprises a computing device programmed to perform operations comprising:
detecting, using the sensor during a first period of time, a first signal;
transmitting, using the transceiver, an indication of the first signal to a remote server;
using the transceiver to receive, from the remote server, cardiovascular classifier information, wherein the cardiovascular classifier information is based on the first signal;
detecting, using the sensor during a second period of time, a second signal;
using a cardiovascular classifier stored in the controller to determine that the second signal is indicative of a cardiovascular event, wherein the cardiovascular classifier is based on the cardiovascular classifier information;
responsive to determining that the second signal is indicative of the cardiovascular event, using the user interface to provide a prompt; and
after using the user interface to provide the prompt, detecting an electrocardiographic waveform from voltage fluctuations between the first electrical contact and the second electrical contact.

2. The wearable device of claim 1, wherein the external body surface is a wrist location of a first arm of a wearer, and wherein the second electrical contact is configured to be contacted by skin of an external body surface of a second arm of the wearer.

3. The wearable device of claim 2, further comprising a modular mount, wherein the modular mount comprises a band and a frame, wherein the housing is configured to be removably seated in the frame, wherein the band is configured to encircle a wrist of the first arm of the wearer, and wherein the second electrical contact is disposed on an outside surface of the modular mount.

4. The device of claim 1, further comprising a further sensor, and wherein the operations further comprise:
detecting, using the further sensor during the first period of time, a third signal;
transmitting, using the transceiver, an indication of the third signal to the remote server, wherein the cardiovascular classifier information is based on the first signal and the third signal; and
detecting, using the further sensor during the second period of time, a fourth signal, wherein using the cardiovascular classifier to determine that the second signal is indicative of a cardiovascular event comprises using the cardiovascular classifier to determine, based on the second signal and the fourth signal, that the second signal is indicative of a cardiovascular event.

5. The device of claim 4, wherein using the cardiovascular classifier to determine, based on the second signal and the fourth signal, that the second signal is indicative of a cardiovascular event comprises:
determining, based on the fourth signal, a particular activity of the user during the second period of time; and
using the cardiovascular classifier to determine, based on the second signal and the determined particular activity of the user during the second period of time, that the second signal is indicative of a cardiovascular event.

6. The device of claim 5, wherein the sensor comprises a photoplethysmographic sensor, and wherein the further sensor comprises at least one of an accelerometer or a gyroscope.

7. The device of claim 1, wherein the sensor comprises at least one of an accelerometer or a gyroscope.

8. The device of claim 1, wherein the sensor comprises a photoplethysmographic sensor.

9. The device of claim 1, wherein the operations further comprise:
   detecting that the first and second electrical contacts are in contact with skin, wherein detecting an electrocardiographic waveform from voltage fluctuations between the first electrical contact and the second electrical contact is performed responsive to detecting that the first and second electrical contacts are in contact with skin.

10. The device of claim 1, wherein the operations further comprise:
    determining, based on the detected electrocardiographic waveform, that the cardiovascular event is occurring; and
    responsive to determining that the cardiovascular event is occurring, using the user interface to provide an indication of the cardiovascular event.

11. The device of claim 1, wherein the operations further comprise:
    transmitting, using the transceiver, an indication of the detected electrocardiographic waveform to the remote server.

12. The device of claim 1, wherein the operations further comprise:
    detecting, using the sensor during a third period of time, a third signal;
    transmitting, using the transceiver, an indication of the third signal to a remote server;
    using the transceiver to receive, from the remote server, an indication of an updated cardiovascular classifier based on the first signal and the third signal;
    detecting, using the sensor during a fourth period of time, a fourth signal;
    using the updated cardiovascular classifier to determine that the fourth signal is indicative of a further cardiovascular event;
    responsive to determining that the fourth signal is indicative of the further cardiovascular event, using the user interface to provide a further prompt; and
    after using the user interface to provide the further prompt, detecting a further electrocardiographic waveform from voltage fluctuations between the first electrical contact and the second electrical contact.

13. A method comprising:
    detecting, using a sensor of a wearable device during a first period of time, a first signal, wherein the wearable device further comprises:
      a housing, wherein the housing is mountable to an external body surface of a wearer;
      a first electrical contact disposed on the housing, wherein the first electrical contact contacts the external body surface when the housing is mounted on the external body surface;
      a second electrical contact;
      a user interface; and
      a transceiver;
    transmitting, using the transceiver, an indication of the first signal to a remote server;
    using the transceiver to receive, from the remote server, cardiovascular classifier information, wherein the cardiovascular classifier information is based on the first signal;
    detecting, using the sensor during a second period of time, a second signal;
    using a cardiovascular classifier stored in the wearable device to determine that the second signal is indicative of a cardiovascular event, wherein the cardiovascular classifier is based on the cardiovascular classifier information;
    responsive to determining that the second signal is indicative of the cardiovascular event, using the user interface to provide a prompt; and
    after using the user interface to provide the prompt, detecting an electrocardiographic waveform from voltage fluctuations between the first electrical contact and the second electrical contact.

14. The method of claim 13, wherein the external body surface is a wrist location of a first arm of a wearer, and wherein the second electrical contact is configured to be contacted by skin of an external body surface of a second arm of the wearer.

15. The method of claim 13, wherein the wearable device further comprises a further sensor, and wherein the method further comprises:
    detecting, using the further sensor during the first period of time, a third signal;
    transmitting, using the transceiver, an indication of the third signal to the remote server, wherein the cardiovascular classifier information is based on the first signal and the third signal; and
    detecting, using the further sensor during the second period of time, a fourth signal, wherein using the cardiovascular classifier to determine that the second signal is indicative of a cardiovascular event comprises using the cardiovascular classifier to determine, based on the second signal and the fourth signal, that the second signal is indicative of a cardiovascular event.

16. The method of claim 15, wherein using the cardiovascular classifier to determine, based on the second signal and the fourth signal, that the second signal is indicative of a cardiovascular event comprises:
    determining, based on the fourth signal, a particular activity of the user during the second period of time; and
    using the cardiovascular classifier to determine, based on the second signal and the determined particular activity of the user during the second period of time, that the second signal is indicative of a cardiovascular event.

17. The method of claim 16, wherein the sensor comprises a photoplethysmographic sensor, and wherein the further sensor comprises at least one of an accelerometer or a gyroscope.

18. The method of claim 13, wherein the sensor comprises at least one of an accelerometer or a gyroscope.

19. The method of claim 13, wherein the sensor comprises a photoplethysmographic sensor.

20. The method of claim 13, further comprising:
    detecting that the first and second electrical contacts are in contact with skin, wherein detecting an electrocardiographic waveform from voltage fluctuations between the first electrical contact and the second electrical contact is performed responsive to detecting that the first and second electrical contacts are in contact with skin.

* * * * *